United States Patent [19]

Faddis

[11] Patent Number: 5,266,275
[45] Date of Patent: Nov. 30, 1993

[54] OZONE STERILIZATION SYSTEM SECONDARY SAFETY CHAMBER

[76] Inventor: Chris G. Faddis, 4221 S. Mark Read St., West Valley City, Utah 84119

[21] Appl. No.: 940,034

[22] Filed: Sep. 4, 1992

[51] Int. Cl.$^5$ ............................................. A61L 2/20
[52] U.S. Cl. .................................... 422/116; 422/28; 422/292; 422/300; 422/305; 422/31; 422/32; 422/33
[58] Field of Search ............... 422/23, 28, 116, 292, 422/300, 305, 31-34, 301; 55/279; 49/31, 340

[56]  References Cited

U.S. PATENT DOCUMENTS

| | | | |
|---|---|---|---|
| 3,753,316 | 8/1973 | Savarieau et al. | 49/31 |
| 3,936,977 | 2/1976 | Runft et al. | 49/340 X |
| 4,552,728 | 11/1985 | Taylor | 422/300 |
| 5,069,880 | 12/1991 | Karlson | 422/186.19 |
| 5,087,419 | 2/1992 | Lutz | 422/28 |
| 5,118,471 | 6/1992 | Andersen et al. | 422/34 |
| 5,120,512 | 6/1992 | Masuda | 422/297 |
| 5,149,500 | 9/1992 | Brahmbhatt et al. | 422/292 X |

Primary Examiner—Robert J. Warden
Assistant Examiner—E. Leigh Dawson
Attorney, Agent, or Firm—M. Reid Russell

[57]  ABSTRACT

In a medical instrument sterilization system that preferably utilizes humidified ozone as a sterilization agent or sterilizing effluent, the system provides for ozone generation, humidification of that ozone and its transfer to for circulation in a primary sterilization chamber wherein medical instruments are scoured clean and sterilized by passage of the humidified ozone therethrough, and for venting the used ozone to a destruction chamber for heat destruction. The invention is in a secondary safety chamber for containing the primary sterilization chamber wherein sterilization operations take place that is locked and sealed during the sterilization cycle and provides for separately sensing and venting for destruction any sterilizing agent as escapes from the primary sterilization chamber.

6 Claims, 4 Drawing Sheets

OZONE STERILIZATION SYSTEM SECONDARY SAFETY CHAMBER

BACKGROUND OF THE INVENTION

1. Field of the Invention

This invention relates to medical instrument sterilization systems, and in particular to sterilization systems that utilize Ozone ($O_3$) as the sterilization.

2. Prior Art

While humidification technologies have long been employed in the field of medical instrument sterilization, and even systems utilizing ozone ($O_3$) as the sterilization agent in such systems have previously been employed, none have provided a separate containment system where the sterilizing agent is circulated to sterilize medical instruments within a primary sterilization chamber that is maintained within a second separate outer safety containment chamber. Nor have such earlier systems monitored conditions in both the primary sterilization chamber and the outer containment or secondary safety chamber to sense and deal with the detection, ventilation, destruction and overall management of transient sterilizing agent as may have inadvertently escaped the primary chamber during sterilization operations. Which structure and features are provided by the present invention.

Some examples of medical equipment sterilization systems that utilize humidification technologies with humidified ozone as the sterilization agent are shown in patents to Masuda, U.S. Pat. No. 5,120,512 and to Karlson, U.S. Pat. No. 5,069,880; and a plurality of containers and chamber arrangements for use in sterilization processes utilizing ozone as the effluent are shown in patents to Anderson, et al, U.S. Pat. No. 5,118,471; and to Lutz, U.S. Pat. No. 5,087,419.

Unlike the present invention, however, none of the above cited earlier systems employ a primary chamber that is the sterilization chamber that is removable in its sealed state for transport to an operating room for opening by medical personnel who use the instruments contained therein. Which primary chamber is maintained, during the sterilization cycle, within a separate secondary safety containment chamber. Also unique to the invention, both the primary and secondary chambers individually connect through humidity sensors that provide for sensing humidified effluent presence, with valves operate for complete venting of the ozone effluent to a destruction chamber prior to allowing opening of the secondary chamber to afford access to the primary chamber. This combination prevents a sterilizing agent release to atmosphere.

SUMMARY OF THE INVENTION

It is a principal object of the present invention in an ozone sterilization system secondary safety chamber to provide a secondary safety chamber for containing a primary sterilization chamber wherein medical instruments are sterilized in a passage of humidified ozone circulated therethrough, the secondary safety chamber for maintaining the primary chamber, is separately sealable, and provides for sensing and venting to a destruction chamber any sterilization agent that is released from which primary chamber.

Another object of the present invention is to provide a secondary safety chamber of an ozone sterilization system for containing the primary sterilization chamber, preventing passage to atmosphere of a sterilization agent as escapes from which primary chamber, provides for venting for destruction of any such escaped sterilization agent, and can be opened for providing access to and removal of which primary chamber only upon sensing of a sterilization agent free atmosphere in both chambers.

Another object of the present invention is to provide, with the secondary safety chamber, an automated capability for sensing a presence of a sterilization agent as has escaped from the primary chamber, and for operating a control system for purging any escaped sterilization agent from the secondary chamber for destruction in a separate sterilization system chamber and for locking against opening until all sterilization agent presence in both the primary and secondary chamber has been removed.

Still another object of the present invention is to provide a sterilization system that is computer controlled to provide, additional to operation of the sterilization cycle in the primary sterilization chamber, for automatically sensing a presence of a sterilization agent in the secondary chamber, for venting and purging such sterilization agent to a destruction chamber, and until both the primary and secondary chambers are empty of sterilization agent, and after delay timers have timed out, prohibiting opening of which secondary chamber.

Still another object of the present invention is to provide a sterilization system console that includes, as a compartment, the separately monitored secondary safety chamber for containing the sterilization primary chamber, which secondary safety chamber provides for venting a sterilization agent, such as ozone, as has escaped from which primary chamber to a sterilizing agent destruction chamber, protecting a health-worker from coming in contact with an escaped ozone effluent.

The invention is in an arrangement of a secondary safety chamber as a compartment in a console that houses a medical instrument sterilization system. The secondary safety chamber is for containing a primary sterilization chamber wherein medical instrument sterilization is performed. The sterilization system preferably utilizes ozone ($O_3$) as a sterilizing agent, and provides for humidifying a flow of ozone passed into and circulated within the primary chamber for sterilizing medical instruments contained therein.

The secondary safety chamber is a compartment in the console housing of the sterilization system that is accessed by a clam shell type lid that is opened by lifting to provide access to the primary sterilization chamber. The closed lid is sealed over the console compartment by operation of an actuator that draws the lid edges against the compartment edges during a sterilization cycle, with individual sensors arranged with the secondary safety chamber for sensing the presence of any sterilizing agent that has escaped from the primary chamber during a sterilization cycle. During the sterilization cycle the secondary chamber is sealed and prior to opening, on sensing a humidified effluent presence by a humidity probe, a valve is opened to vent the sterilization agent to a destruction chamber for heating to destruction. Conditions within the primary chamber are monitored by a separate humidity probe.

The sterilization cycle is computer controlled and after completion, any sterilization agent or ozone effluent found in either the primary or secondary chambers is vented through valves for destruction, in the destruction chamber. Upon verification that the primary and secondary chambers are free of effluent, and after a timed period, air under pressure that has been routed to a pneumatic actuator in the secondary chamber is shut off, allowing for pivoting of the lid out of sealed engagement over the console compartment, exposing the primary sterilization chamber that contains the sterilized medical instruments for removal and transport to an operating theatre.

BRIEF DESCRIPTION OF THE DRAWINGS

In the drawings that illustrate that which is presently regarded as the best mode for carrying out the invention.

DETAILED DESCRIPTION

Figure 1:
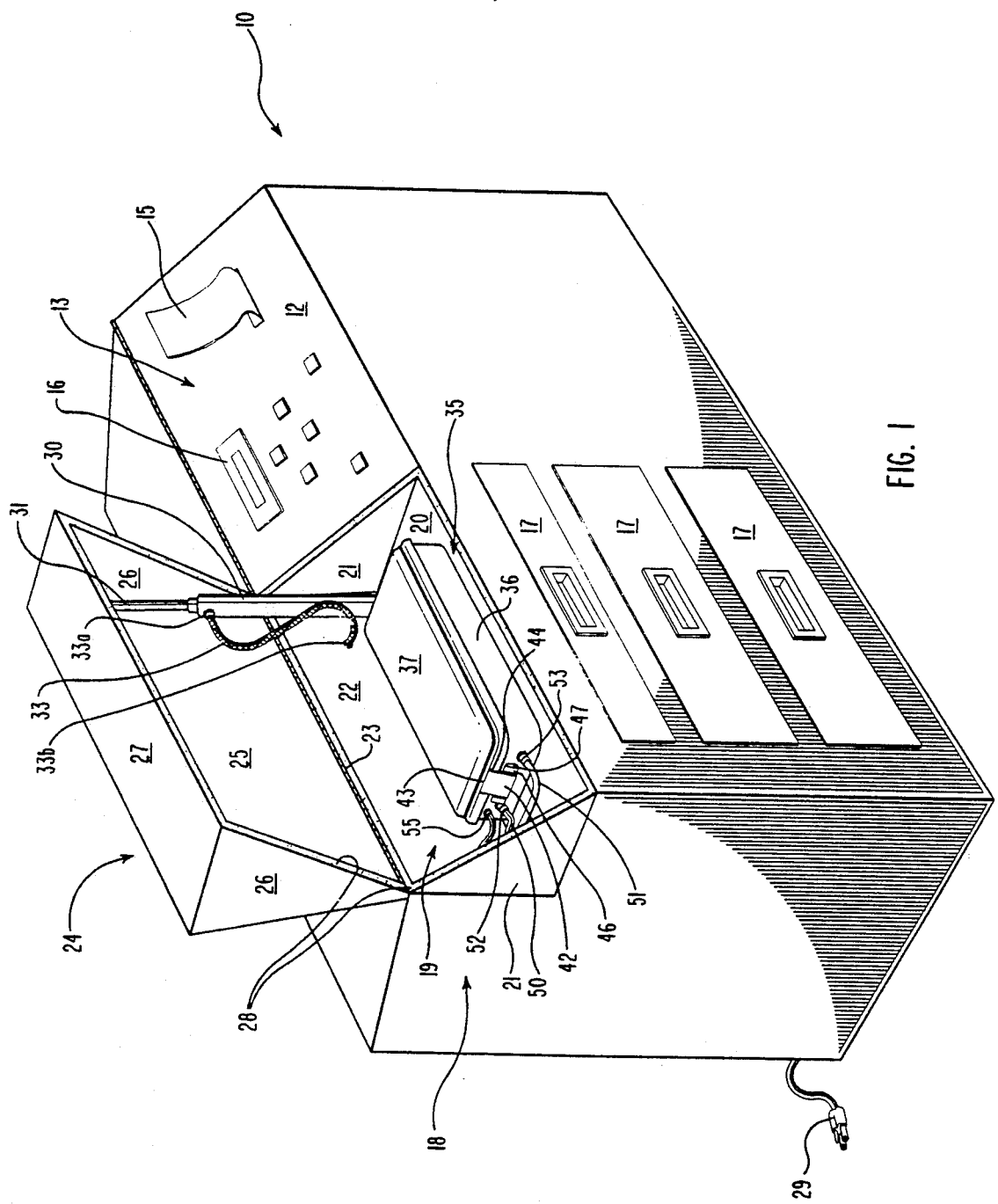
FIG. 1 is a profile perspective view of a console containing an ozone sterilization system, with a clam shell type lid that is for covering a top section of the console shown in an open attitude exposing a compartment that is a secondary safety chamber of the invention that contains a primary sterilization chamber wherein medical instrument sterilization takes place.
Figure 2:
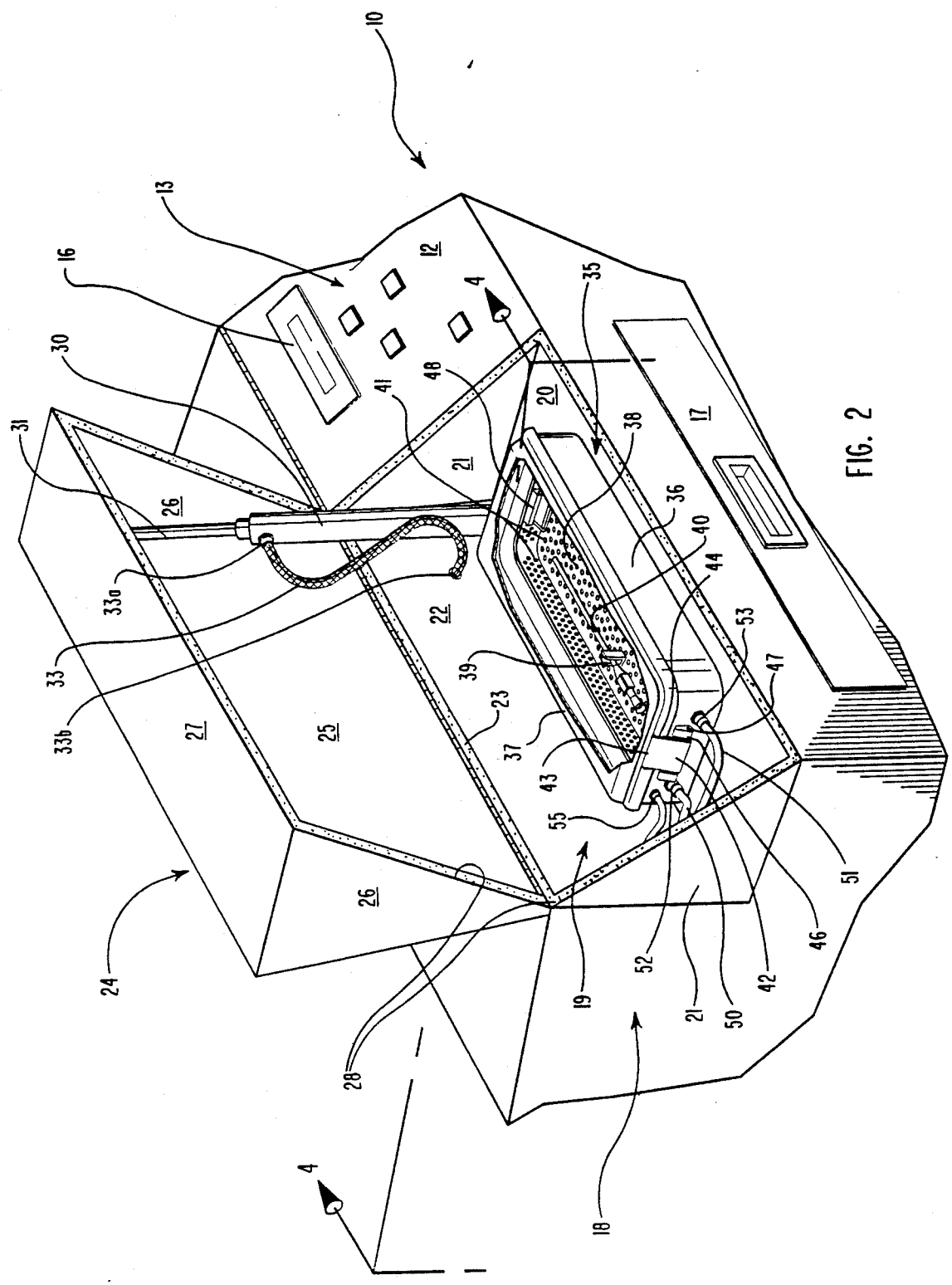
FIG. 2 is an enlarged view of a section of the console of FIG. 1, showing the clam shell type lid that includes a pneumatic piston arrangement for lowering and retarding opening of which lid, and showing a section of the primary sterilization chamber lid broken away exposing a pan wherein medical instruments are arranged for sterilization.

FIG. 1 shows a console 10 that contains, as shown in the block flow schematic view of FIG. 3, a medical instrument sterilization system 11, hereinafter referred to as sterilization system, that utilizes ozone (O₃) as the sterilizing agent. In FIGS. 1 and 2, a sloping right side 12 of the console 10 is shown to include a control panel 13. The control panel 13, as shown also in the schematic of FIG. 3, includes a number of buttons connecting through a programmable logic circuit (PLC) 14, that is shown also in FIG. 5. The control panel 13 buttons are for use by an operator who provides an input into the sterilization system 11 operation, with the programmable logic circuit (PLC) 14 processing that input to operate the system components, as set out below. During which system operation a printer 15 is connected to produce an output from the programmable logic circuit 14, for providing a printed record of system operation. A display 16 is shown arranged with which control panel 13 for providing a display or system readouts and time.

Figure 4:
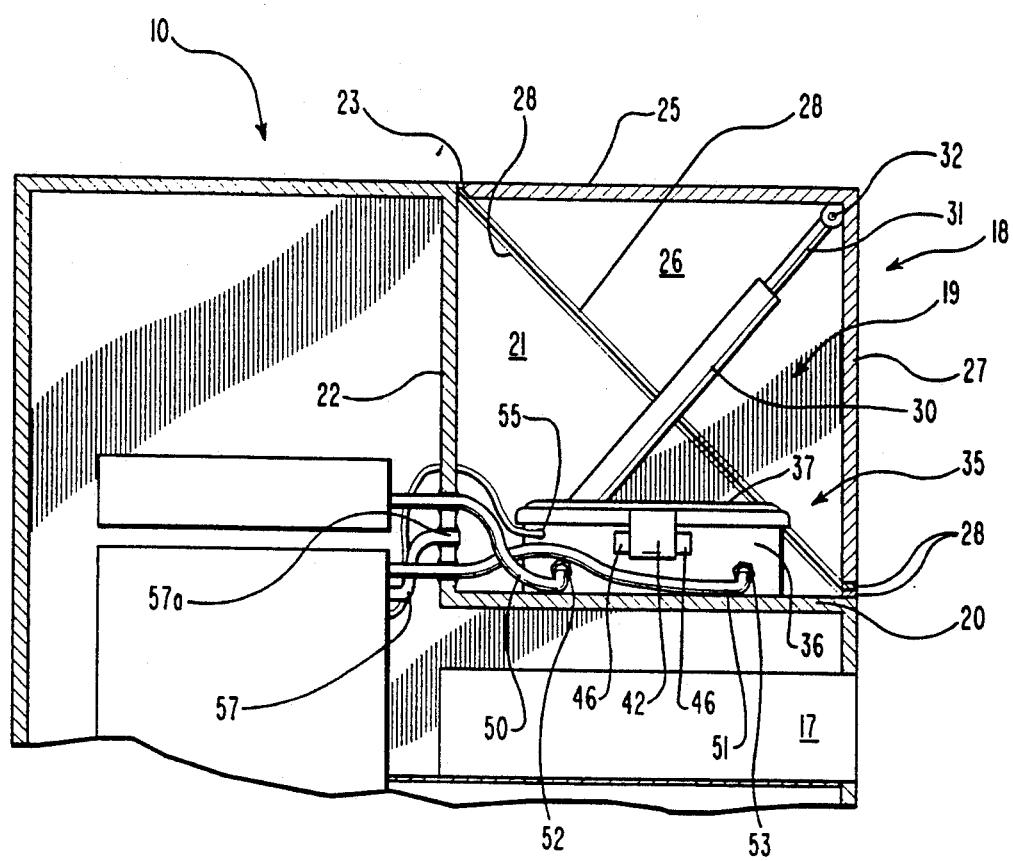
FIG. 4 is a side elevation sectional view taken along the line 4—4 of FIG. 2, only showing the clam shell type lid closed over the compartment.

As shown in FIG. 1, the left side of console 10, in a lower section thereof, includes a stack of drawers 17, for storage of system accessories, tools, and the like, and an electrical plug 29 is shown for connecting the system to a source of electricity. FIGS. 1, 2 and 4, show a secondary safety chamber 18 of the invention, hereinafter referred to as secondary chamber, formed as a rectangular console compartment 19 that is located in the top left side thereof, alongside of the control panel 13.

The compartment 19, with a clam shell type lid 24 fitted thereon, has a rectangular shape with identical flat bottom 20, and top 25, with right angle back and front walls 22 and 27 respectively, and side walls that are cut on the bias into sections 21 and 26, respectively. A top edge of the back wall 22 is connected through a hinge 23 to a rear edge of top 25. The clam shell type lid 24, hereinafter referred to as lid, is thereby formed by the top wall 25, side wall sections 26 and front wall 27, respectively. Lid 24 is a complement to the compartment 19 bottom portion that consists of bottom 20, side wall sections 21 and back wall 22. The lid 24 side wall sections 26 and front wall 27, respectively, edges are flush with and engage the edges of which compartment bottom portion side wall sections 21, back wall 22. Which compartment walls and the console are preferably formed of steel panels with the joints sealed, though other suitable material could be used in their construction within the scope of this disclosure. Seals 28 are provided along the lid and compartment opposing surfaces for contacting one another when the lid 24 is closed, as shown in FIG. 4, for sealing the compartment 19 interior off from the surrounding area. Which seals 28, in practice, are preferably silicon sheet, and a preferred silicon sheet is a product known as Silastic, manufactured by General Electric Corporation.

The secondary chamber 18 is to be maintained in a closed sealed attitude during a sterilization cycle. To provide which locking, an actuator 30, that may to hydraulic or pneumatic, but is preferably pneumatic, is pivotally coupled at one end to the compartment 19 bottom 20 and includes a rod 31 extending outwardly from its opposite end. The rod end within the actuator 30 is secured to a piston, not shown, and is pivotally coupled on its opposite end at 32 to the junction of the lid top 25 and front wall 27, as shown best in FIG. 4. A pressure hose is shown in FIGS. 1 and 2 connected at one end 33a into the actuator 30, proximate to the end wherefrom the rod 31 extends, and is fitted through the compartment 19 back wall 22 at 33b to connect to a source of air under pressure, not shown When the sterilization system 10 is not in operation, the compressed air in the actuator acts as a brake against rod 31 travel, affording resistance to travel by an operator lifting or lowering the lid 24, pivoting around the hinge 23. When the sterilization system 10 is in operation, air under pressure is available in the actuator 30, acting against the piston to urge the rod 31 into which actuator, to pull the lid 24 edges into close fitting contact with the compartment bottom portion edges, compressing the seal 28. The compartment interior is thereby sealed against leakage to atmosphere so long as the sterilization cycle is in process and so long as sterilization agent or effluent presence is sensed in the secondary chamber 18 or in a primary sterilization chamber 35, as set out hereinbelow.

As shown in the drawings, the secondary chamber 18 contains the primary sterilization chamber 35, hereinafter referred to as primary chamber. Shown best in FIGS. 1, 2 and 4, the primary chamber 35 is preferably a rectangular pan 36 with an open top for covering by a lid 37, and, as shown best in FIG. 2, contains an instrument holding tray 38, hereinafter referred to as tray. Tray 38 may include an instrument mount 39 or mounts, for holding an instrument 40 during its sterilization, or may have a flat bottom surface, within the scope of this disclosure. All of which components are preferable formed from a rigid material, such as stainless steel, that is not affected by the sterilization agent or effluent, that is preferably humidified ozone, and is used in the sterilization process carried on in which primary chamber 35. Preferably the tray 38 has a number of holes 41 formed through its bottom and side walls for promoting circulation of a sterilizing agent in, around and through the instrument 40, thoroughly cleaning and sterilizing all of the instrument 40 surfaces and crevices.

The lid 37 is for fitting, in sealing engagement, over the pan 36 during a medical instrument sterilization cycle and during transport of the primary chamber 35 containing sterilized medical instruments to an operating room wherein the seal is broken by operating room personnel, as discussed hereinbelow. To provide this sealed engagement, the opposing lid and pan edges are formed to overlay one another, fitting closely together, and, as needed, a seal is arranged between which opposing edges for providing an air tight seal when the edges are compressed together. Which seal is formed of a material that is not reactive with ozone, such as a silicon sheet material, and a preferred silicon sheet is a product known as Silastic, manufactured by General Electric Corporation. In practice, as set out above, a preferred sterilization agent or effluent is ozone gas that has been humidified after formation and is at or near atmospheric pressure and standard or room temperature. Accordingly, the seal in both the primary and secondary chambers 35 and 19 is not required to contain high pressures or temperatures.

To provide for compressing the lid and tray edges together, pan handles 42 are provided on opposite pan ends. Each pan handle 42 includes a hook 43, or bent over end, that is for fitting into a groove 44 that is formed into the center of an end section of a step that is formed around the lid 37. Each handle 42 opposite end is arranged for pivot coupling to a pan end and is bent upon itself into a tube end, not shown. A pin 47 is fitted through the handle tube end, not shown, and through aligned holes or openings that are formed through a pair of piers 46 that are secured to and extend outwardly from the pan ends. So arranged, each handle 42 is free to pivot around pin 47 coupling with the pan 36 end, and is bowed outwardly across its center such that an operator can apply pressure to the bow, to flex it inwardly to where its hook end 43 will slid over the lid edge and into the groove 44. Whereafter, the operator releases pressure on the handle 42 that will then return to its original bowed state, drawing the hook end 43 into which lid edge groove 44, and pulling which lid edge into sealing engagement with the pan edge. The handles 42 pivot couplings through pins 47 that are maintained across piers 46 also provide gripping surfaces for facilitating an operator lifting the primary chamber 35 out from the secondary chamber 18 and carrying it to an operating room. After transport to such operating room, the handles 42 are bent inwardly against their bow, releasing the lid 37, to expose the tray 38 therein. Which tray 38 is shown as including pivoting handles 48 secured to opposite ends for gripping for lifting the tray out from the primary chamber 35.

Medical instrument sterilization takes place in the primary chamber 35 that is arranged to be removable from the secondary chamber 18 for transport in a sealed state to an operating room. Accordingly, both a sterilizing agent inlet line 50 and an exhaust line 51, as shown also in FIG. 5 as effluent in and effluent out lines, are connected into the primary chamber pan 36 by quick release couplings 52 and 53, respectively. Which quick release couplings may be any appropriate quick release coupling where the primary chamber remains sealed after disconnection but are preferably standard pneumatic hose type couplings where a male member that is secured to the end of the inlet or exhaust lines 50 or 51 is fitted into a female member secured across an opening into the pan 36. Which female member includes a spring loaded collar that is arrangement for movement away from the male member, against its spring biasing, to release a ball contained in which female member to pass into a groove formed around which male member. With release of the female member collar the spring biasing returns the collar to its original attitude where the ball is prohibited from rolling out of the male member groove, locking the male and female members together. In operation, when the male member is released out of the female member, by moving the collar away from which male member, the opening through the female member is automatically closed.

Figure 5:
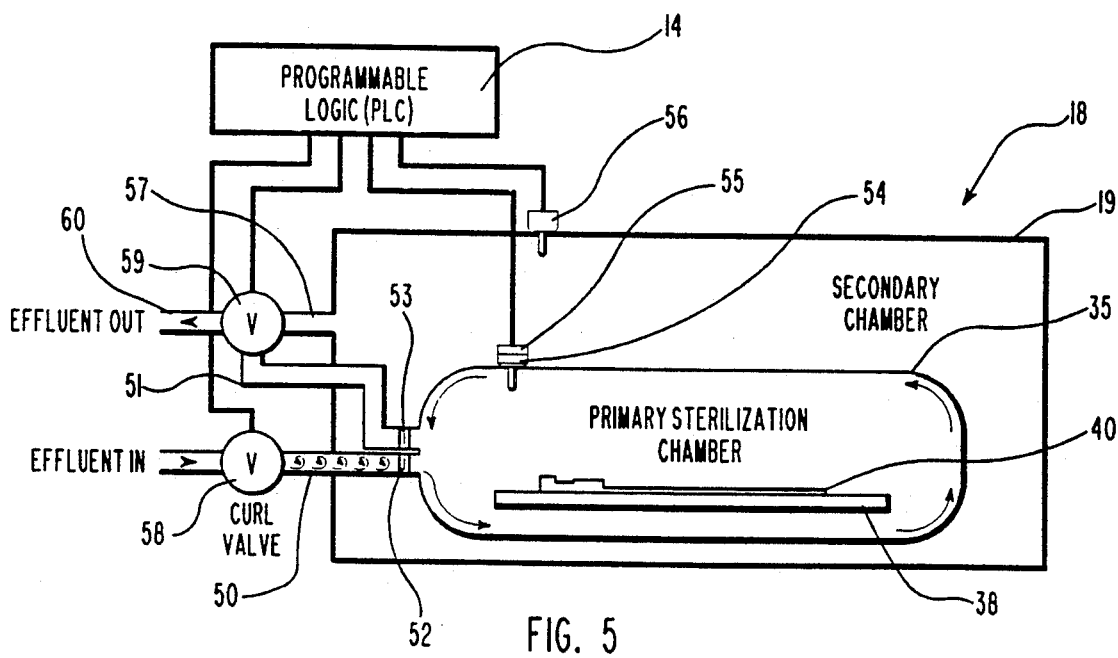
FIG. 5 is a side elevation schematic of the secondary safety chamber containing the primary sterilization chamber and showing sensors and gas valves for operation by a programmable logic circuit.

Humidity probes or sensors 54 and 56, respectively, are provided for sensing humidified sterilization agent presence in the primary and secondary chambers, 35 and 18, respectively, by sensing humidity in which chambers. Within the scope of this disclosure the humidity probes or sensors 54 and 56 can be physically mounted in the primary and secondary chamber, 35 and 18, respectively, as shown best in FIG. 5, or can be arranged in the primary chamber exhaust line 51 and a secondary chamber exhaust line 57, as shown best in FIG. 3. Shown best in FIG. 4, the secondary chamber 18 exhaust line 57 end 57a is mounted in the secondary chamber back wall 22 wherethrough the primary chamber inlet and exhaust lines 50 and 51 are fitted and sealed. Both of which exhaust lines 51 and 57 connect into an effluent out line 60, as shown in FIGS. 3 and 5. Where the primary chamber 35 humidity probe or sensor 54 is for mounting into the pan 36, as shown in FIG. 5, it includes a base that extends beyond the pan surface. Which base is preferably a female electrical plug that is arranged for receiving and electrically coupling to a male electrical coupling 55 that is connected by wire, as is the secondary chamber humidity probe or sensor 56, into the programmable logic circuit (PLC) 14. Chamber humidity readings are thereby provided to the PLC 14 that are utilized for controlling the sterilization cycle and chamber venting. The quick disconnect inlet and exhaust line couplings 52 and 53, respectively, and the humidity probe or sensor 54 and male coupling 55, facilitate the removal of the primary chamber 35 from the secondary chamber 18 after sterilization. The primary chamber 35 containing sterilized medical instruments can then be transported, in a sealed state, to an operating room for opening by medical personnel. The primary chamber 35 is therefore both a sterilization vessel and transport container. For these duel roles, the primary chamber pan 36, lid 37 and tray 38 are preferably formed from an appropriate ridged material, such as stainless steel, that is not effected by the preferred sterilizing agent humidified ozone and is convenient to carry, utilizing handles 42, to an operating room or theater.

Hereinabove has been set out a full description of the present invention in a secondary chamber 18 and its functioning in a sterilization cycle that is carried on in the primary sterilization chamber 35 contained in which secondary chamber. As set out, the sterilization cycle is automated under the control of the programmable logic circuit (PLC) 14 with an operator inputting information at control panel 13 buttons, with system functions displayed at display 16. On starting the sterilization cycle, as illustrated in FIG. 5, the PLC 14 opens valve 58, identified as effluent in, passing and circulating humidified ozone to within the primary chamber 35. At the conclusion of which sterilization cycle, the PLC 14 operates an effluent out, valve 59 to vent both the primary and secondary chambers 35 and 18 through their respective exhaust lines 51 and 57, into an effluent out line 60. In practice, the respective primary and secondary chamber humidity probes or sensors 54 and 56 must sense an absence of the humidified sterilization agent in both of the chambers before the PLC 14 will release the actuator 30, allowing for opening of the secondary chamber lid 24, for removal of the primary chamber 35.

Figure 3:
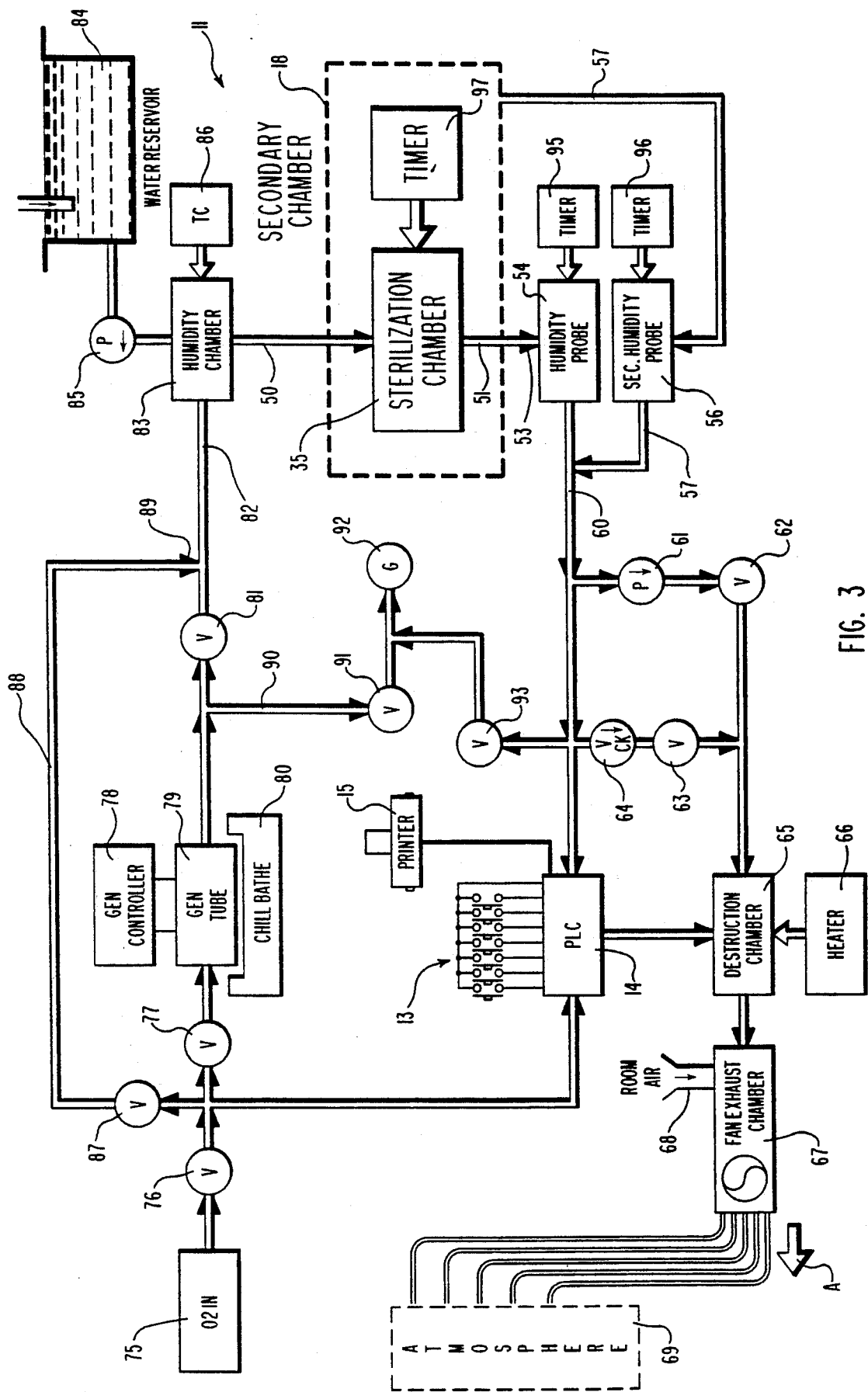
FIG. 3 is a block flow schematic of the ozone sterilization system showing the secondary safety chamber in broken lines.

In the effluent venting process, as illustrated by the block flow schematic of FIG. 3, effluent from the primary and secondary chambers 35 and 18 is pulled through the effluent out line 60 by pump 61, that flow passing through valve 62 and into a destruction chamber 65. Additionally, for controlling effluent passage for destruction, the effluent out line 60 connects to the PLC 14 for provide a sensing of effluent presence, and is joined to an ozone emergency venting line 90. Which line 90 extends from an ozone generation tube 79 that connects through valves 91 and 93 and contacts an in line pressure gauge 92 that provides data to the PLC 14. The junction of the effluent out line 60 with the ozone emergency venting line 90 connects through a check valve 64 and valve 63 to vent ozone and humidified ozone into the destruction chamber 65. The destruction chamber 65, in turn, utilizes a heater 66 to heat the received humidified ozone or ozone alone, breaking down the received ozone into an inert state, that is pulled by a fan into a fan exhaust chamber 67. The fan exhaust chamber mixes the received oxygen with room air that enters through port 68 and the mixture is then vented, illustrated by arrow A, to atmosphere, as shown as a broken line box 69. So arranged, an operator is protected from a sterilization agent exposure both during the sterilization cycle and during venting operations.

The venting cycle, as set out above, is for safely purging all sterilization agent from the primary chamber 35 and from the secondary chamber 18. Which sterilization agent or effluent, as set out above, is preferably a humidified ozone mixture. For producing this humidified ozone gas flow, as illustrated in FIG. 3, oxygen, shown as block 75, is passed through valves 76 and 77 into a generation tube 79. As shown, the generation tube 79 is controlled by a generation controller 78 and is maintained within a chill bathe 80 for maintaining the produced ozone at or near atmospheric pressure and room or standard temperature conditions.

On opening of valve 81, ozone from generation tube 79 passes through line 82 to a humidity chamber 83. A water reservoir 84 is provided for supplying water, under pressure, from a pump 85, to the humidity chamber 83. A temperature control 8 is provided for maintaining a desired temperature of ozone and water vapor in humidity chamber 83. Which temperature, in practice is thirty one (31) degrees Centigrade (C) for maintaining a desired ozone concentration of approximately twelve (12) percent, with ten (10) percent water to oxygen, plus or minus three (3) percent, that is produced by spraying water under pressure through a nozzle in which humidity chamber 83. The humidified ozone is passed from humidity chamber 83 through line 50 into the primary sterilization chamber 35, as set out hereinabove. Which humidified ozone is accordingly at or near atmospheric pressure and at room or standard temperature, greatly simplifying sterilization operations as the primary chamber 35 is required only to maintain low temperature and pressure of gas, simplifying the sealing requirements of both the primary and secondary chambers 35 and 18, respectively.

For start-up, and for controlling ozone concentrations during operations, valve 87 may be opened for routing oxygen around the ozone generation tube 79. With valve 87 open, oxygen passes through line 88 to junction 89 with line 82, passing oxygen to the humidity chamber 83. Oxygen may therefore also be conveniently utilized for providing system purging after suspension of ozone generation. In the event of a termination of the sterilization cycle prior to completion, it is, of course, necessary to remove the ozone sterilization agent from the system. This is accomplished by shutting down the ozone generation tube 79 and closing valve 81. In which shut down state oxygen is preferably routed, as set out above, to the humidity chamber 83. The ozone generator is thereby bypassed, to purge the sterilization chamber 35. For venting ozone as is present in the generation tube 79 and connecting lines, through a line 90, a valve 91 is opened and ozone presence in the generation tube and lines is monitored by pressure gauge 92. Opening of valve 93 allows for continued effluent passage in line 90 to both the PLC 14, for monitoring and control, and through the check valve 64 and valve 63 for destruction in the destruction chamber 65, as set out above.

Timers 95 and 96 are provided for monitoring component operations during a sterilization cycle that are connected, respectively, to the humidity probe 54, that senses humidified ozone presence in the sterilization chamber 35, and to secondary humidity probe 56, that monitors humidified ozone presence in the secondary chamber 18. The timers 95 and 96 are started when the humidity probes indicate an absence of humidified ozone, for continuing the system purging for a period of time to insure a full evacuation of humidified ozone from the primary and secondary chambers prior to system opening. Further, a timer 97 is provided that is set by an operator to a time period of the sterilization cycle for the particular medical instruments to be sterilized. Which primary sterilizer chamber timer 97 is programed and that setting is passed to the PLC 14 for setting the periods for system component functioning.

While a preferred form and embodiment of my invention in an ozone sterilization system secondary safety chamber and its functioning within an ozone sterilization system has been shown and described herein it should be understood that the present disclosure is made by way of example only, and that variations and changes can be made thereto without departure from the subject matter coming with the scope of the following claims, and a reasonable equivalency thereof, which claims should be regarded as my invention.

I claim:

1. A secondary safety chamber as a component of a medical instrument sterilization system comprising: a sterilization agent; a sterilization system housing that contains a compartment as a secondary safety chamber that includes a first lid means for closing and sealing said secondary safety chamber from the atmosphere; a primary sterilization chamber housed within said secondary safety chamber, said primary sterilization chamber including a separate second lid means for separately closing and sealing said primary sterilization chamber as a sterilization system, with sterilization agent inlet and outlet lines fitted and sealed through walls of said secondary safety chamber and connecting into said primary sterilization chamber, said first lid means is arranged for fitting over an opening into said compartment; means for sealing said compartment when said first lid means is fitted thereto; means for locking said first lid means in its sealed attitude covering said compartment opening during a sterilization cycle and until released; a sterilization agent out line that is separate from said sterilization outlet lines connected into said secondary safety chamber, for venting sterilization agent as escapes from said primary sterilization chamber to a destruction chamber; valving means for regulating the flow of sterilization agent in said sterilization agent inlet line and for venting sterilization agent from the chambers; and means for sensing a presence of said sterilization agent in said secondary safety chamber, said sensing means utilized for controlling the sterilization cycle and the chamber venting.

2. A secondary safety chamber as recited in claim 1, wherein the compartment and first lid means closed over which compartment opening that form the secondary safety chamber have a rectangular shape interior area, and said first lid means includes a flat top and front wall at a right angle thereto, with a pair of identical sides that are each formed at right angles to which top and front wall and are cut on the bias to provide edges that fit to the edges of sloping compartment sides, which said first lid means is hinge connected along its top edge opposite to its coupling to front wall to a top edge of a compartment rear wall; and strips of seal material are secured across said first lid means and compartment hinge coupling, the bottom edge of said first lid means front wall, and a forward edge of a compartment bottom, providing, with said first lid means locked over the compartment, for sealing the compartment against leakage of a sterilization agent therefrom.

3. A secondary sterilization chamber as recited in claim 2 wherein, the means for locking the first lid means in a sealed attitude covering the compartment opening is a pneumatic actuator that consists of a cylindrical body with a rod telescoped out from one end thereof with the other actuator end pivotally mounted within the compartment, and said actuator rod end is pivotally coupled to said first lid means and said actuator rod end is fitted into said actuator cylindrical body and includes a piston means secured thereto that travels up and down in said actuator cylindrical body; and means for providing air under pressure directed into said actuator cylindrical body that will act against said piston to urge said connected rod into said actuator cylindrical body, drawing said lid therewith into close fitting contact with the edges of said compartment.

4. A secondary sterilization chamber as recited in claim 1, wherein, the sterilization agent out line connects on one end into the secondary sterilization chamber wall with the opposite end connected into a valve that, when opened, connects into a common line with the primary sterilization chamber sterilization agent out line, that passes vented sterilization agent to a destruction chamber for exposure to heat to render said sterilization agent inert.

5. A secondary sterilization chamber as recited in claim 4, wherein, a humidity detector mounted in the sterilization agent out line from the secondary sterilization chamber as the means for sensing the presence of a sterilization agent; and timer means that is programmed by an operator to provide a time period for continued sterilization cycle operation after said humidity detector has ceased detecting the presence of humidified sterilization agent.

6. A secondary sterilization chamber as recited in claim 1, wherein a humidity detector is connected into the secondary sterilization chamber as the means for sensing the presence of a sterilization agent.

* * * * *